United States Patent [19]
Dingley

[11] Patent Number: 5,979,443
[45] Date of Patent: Nov. 9, 1999

[54] CLOSED VENTILATION/ANESTHESIA APPARATUS

[75] Inventor: John Dingley, Swansea, United Kingdom

[73] Assignee: University of Wales College of Medicine, Cardiff, United Kingdom

[21] Appl. No.: 08/973,634

[22] PCT Filed: Jun. 10, 1996

[86] PCT No.: PCT/GB96/01392

§ 371 Date: Dec. 5, 1997

§ 102(e) Date: Dec. 5, 1997

[87] PCT Pub. No.: WO96/41651

PCT Pub. Date: Dec. 27, 1996

[30] Foreign Application Priority Data

Jun. 8, 1995 [GB] United Kingdom .................. 9511651

[51] Int. Cl.⁶ .......................... A61M 16/00; A62B 7/04; F16K 31/26
[52] U.S. Cl. ................. 128/204.28; 128/204.26; 128/205.13; 128/205.14; 128/205.15
[58] Field of Search .............. 128/204.18, 204.26, 128/204.28, 205.12, 205.13, 205.14, 205.15, 205.16, 205.17, 205.27, 205.28

[56] References Cited

U.S. PATENT DOCUMENTS

| | | | |
|---|---|---|---|
| 3,307,542 | 3/1967 | Andreasen | 128/205.15 |
| 3,789,837 | 2/1974 | Philips et al. | 128/203.26 |
| 3,831,595 | 8/1974 | Valenta et al. | 128/145.8 |
| 3,973,564 | 8/1976 | Carden | 128/205.14 |
| 4,256,100 | 3/1981 | Levy et al. | 128/204.21 |
| 4,423,723 | 1/1984 | Winkler et al. | 128/202.22 |
| 4,498,470 | 2/1985 | Warnke | 128/202.26 |
| 4,883,051 | 11/1989 | Westenskow et al. | 128/204.21 |
| 4,909,246 | 3/1990 | Kiske et al. | 128/205.14 |
| 4,991,576 | 2/1991 | Henkin et al. | 128/203.28 |
| 5,490,499 | 2/1996 | Heinonen et al. | 128/203.28 |

FOREIGN PATENT DOCUMENTS

| | | | |
|---|---|---|---|
| 1237217 | 6/1960 | France | 128/205.13 |
| 2619435 | 11/1977 | France | 128/205.15 |
| 1031049 | 5/1963 | United Kingdom | 128/205.15 |
| 1237273 | 6/1971 | United Kingdom | 128/205.15 |
| 9003820 | 4/1990 | WIPO . | |

OTHER PUBLICATIONS

Mannesmann Rexroth, Technical Information, Pneumatic Symbols, 1996.

William W. Mushin et al., *Automatic Ventilation of the Lungs*, Chapter 14 (pp. 285–294) Blackwell Scientific Pub. (3d Ed. 1980).

*Primary Examiner*—John G. Weiss
*Assistant Examiner*—Joseph F. Weiss, Jr.
*Attorney, Agent, or Firm*—Edwin D. Schindler

[57] ABSTRACT

An inhalation apparatus, which supplies appropriate volumes of oxygen to a closed breathing system, to replace the oxygen used by a patient. A variable volume enclosure is situated within a container, which has an inlet connected to a ventilator for the supply of oxygen into the container. The interior of the variable volume enclosure is in communication with the breathing system, and the interior of the container is also in communication with the breathing system, via a one-way valve, which opens to replenish the oxygen in the breathing system, when the pressure in the breathing system is lower than that within the container.

14 Claims, 7 Drawing Sheets

CLOSED VENTILATION/ANESTHESIA APPARATUS

BACKGROUND OF THE INVENTION

1. Technical Field of the Invention

This invention relates to an inhalation apparatus which may be used in the measurement of the volume of a patient's blood, or which may be used as a closed anaesthetic system.

2. Description of the Prior Art

It is often necessary, particularly in the case of critically ill patients in an intensive care unit, to measure the patient's blood volume in order to assess the need for a blood transfusion. One of two generally-used methods involves the measurement of red-cell volume and subsequent calculation of total blood volume from the haematocrit, the other involves the measurement of plasma volume and again subsequent calculation of total blood volume from the haematocrit. Often both methods are used and total blood volume is then obtained by adding the measured red-cell and plasma volumes.

An established method of measuring red-cell volume involves the steps of removing a small sample of blood from the patient, labelling the red cells in the sample with radioactive tracers, and re-injecting the radio-labelled sample into the patient. After a predetermined period of time, the sample will have mixed evenly with all of the blood in the patient's body. Another sample of blood is then removed and the "dilution" of the radioactive tracers is determined, which enables the volume of blood into which the sample was re-injected to be calculated, and hence the blood volume of the patient may be determined.

The above method has been established as a sufficiently accurate method of indicating blood volume, involving relatively simple procedures and using standard equipment. However, this method is time consuming and expensive and cannot be repeated at frequent intervals: therefore, if an error occurs, it may be some time before the test can be performed again. This also means that it is not possible to monitor a patient's blood volume at frequent intervals, which may be required under certain circumstances. Another drawback of the method is that it involves radioactivity, which can be hazardous.

Another known method of measuring red-cell volume again involves the steps of removing a small sample of blood from the patient, labelling the red cells in the sample, and re-injecting the labelled sample into the patient. However, in this case, the red cells are labelled with a small quantity of carbon monoxide (CO) which is injected into the sample of blood. Carbon monoxide binds to haemoglobin in red blood cells to form carboxyhaemoglobin. Thus, once the re-injected sample has been allowed sufficient time to mix evenly with the blood in the patient's body, the "dilution" of the carboxyhaemoglobin in the patient's blood, and subsequently the blood volume, may be determined.

Although the above-described method eliminates the hazards of using radioactivity, it is still time-consuming and cannot be repeated at frequent intervals: it moreover involves the risk of infection to the medical staff handling the blood samples at the bedside. A more convenient method of measuring blood volume has been proposed wherein carbon monoxide saturation of a patient's haemoglobin or carboxyhaemoglobin is first measured and the patient then inhales a small known quantity of carbon monoxide which crosses to the red blood cells through the lungs. The carboxyhaemoglobin is again measured and the total quantity of haemoglobin may thereby be calculated which, in turn, allows calculation of the patient's blood volume. Patients in intensive care units are usually unable to breathe unaided and are thus ventilated artificially by means of a tube passed into the trachea (endotracheal tube). It is therefore necessary to provide apparatus for ventilating the patient artificially whilst administering the required dose of carbon monoxide. Such an apparatus is shown in FIG. 1 of the drawings and comprises an elongate pipe 100 connected at one end via a connector 102 to the endotracheal tube, through which the patient is ventilated. A carbon dioxide ($CO_2$) absorber 104 is provided in the pipe 100, downstream of the mouthpiece 102, and a filter 106 is also provided for preventing dust from the $CO_2$ absorber 104 entering the patient's airways. The apparatus further comprises an oxygen sensor 108, a 2-1 rebreathing bag 110, a first inlet 112 having a one-way valve (not shown) for administering oxygen, and a second inlet 114 having a one-way valve (not shown) for administering the carbon monoxide.

Initially, the rebreathing bag 110 is filled with approximately 2 liters of oxygen and the connector 102 is attached to the endotracheal tube. The rebreathing bag is manually squeezed and the oxygen therein is forced through the pipe 100 and out through the connector 102 to the endotracheal tube to inflate the patient's lungs. Air is automatically exhaled from the lungs by the passive recoil of the chest of the patient and enters the pipe 100 from the endotracheal tube via the connector 102. Carbon dioxide in the exhaled air is absorbed by the $CO_2$ absorber 104 so that substantially pure oxygen re-enters the rebreathing bag 110, thereby inflating it once again. The procedure described above is repeated in order to ventilate the patient and the oxygen sensor 108 ensures that the patient is receiving sufficient oxygen. As the patient is ventilated, some of the oxygen passed into the patient's lungs is used up thereby: the quantity of oxygen within the rebreathing bag 110 therefore diminishes over a period of time. Human lungs use approximately 250 ml of oxygen per minute. In order to top up the bag 110, oxygen is manually introduced into it via the one-way valve in the inlet 112 at approximately 250 ml per minute. For the purpose of measuring blood volume, a small known quantity of carbon monoxide is introduced into the pipe 100 via the one-way valve in the inlet 114. When the rebreathing bag 110 is squeezed, the carbon monoxide is passed into the patient's lungs along with the oxygen. When the patient exhales, any carbon monoxide which has not crossed the lungs is forced back into the apparatus via the connector 102 together with the rest of the exhaled air. However, carbon monoxide is not absorbed by the $CO_2$ absorber: therefore, when the bag 110 is squeezed again, any carbon monoxide which has not crossed the patient's lungs is 'rebreathed' together with the oxygen. This procedure is repeated until all of the carbon monoxide has been absorbed by the patient's lungs: this usually takes about 15 minutes.

A number of problems occur in use of apparatus of FIG. 1. Firstly, it is inconvenient to have to repeatedly squeeze the rebreathing bag for as long as 15 minutes to manually ventilate the patient. Secondly, it is necessary to manually top-up the oxygen in the rebreathing: this may lead to errors and thus insufficient oxygen reaching the patient, which is clearly dangerous. Thirdly, over-zealous inflation of the patient's lungs may cause air and carbon monoxide to escape past the cuff of the endotracheal tube into the trachea, which would cause the results of the test to be inaccurate. Further, a single dose of carbon monoxide is administered through the one-way valve in inlet 114 by means of a syringe: thus the valve must allow removal of the syringe without permitting any carbon monoxide to escape; if a leak occurs in the one-way valve, carbon monoxide will be allowed to escape, leading to inaccurate results.

We have now devised an inhalation apparatus which may be used for blood volume measurement, and enables the problems outlined above to be overcome.

In the case of anaesthetic systems, it is usual for a predetermined mixture of anaesthetic vapour and oxygen to be supplied from an anaesthetic supply unit to a "circle" which includes a carbon dioxide absorber, one-way valves and a connector to the tracheal tube. A ventilator is connected into the circle and alternately supplies oxygen to the circle, causing inflation of the lungs, and then vents to atmosphere (for exhaled gas to pass into the atmosphere). The patent does not absorb all of the anaesthetic vapour on each inspiration, and accordingly some of the anaesthetic vapour is vented to atmosphere upon exhalation. Accordingly, some of the anaesthetic substance (which is expensive) is wasted, and furthermore pollutes the atmosphere.

We have now devised an inhalation apparatus which may be used as an anaesthetic system to overcome the foregoing problems.

SUMMARY OF THE INVENTION

In accordance with the present invention, there is provided an inhalation apparatus which comprises a closed breathing system having a port for coupling to a patient and an inlet for introduction of a gas or vapour, and a ventilating system comprising a sealed variable volume enclosure situated within a container, said container having an inlet for introducing oxygen into said container, the interior of said enclosure being in communication with said breathing system and the interior of said container being in communication with said breathing system via a one-way valve.

In use, oxygen is introduced into the container. This increases the pressure outside the variable-volume enclosure, and causes contraction of the latter so that the oxygen within the enclosure is passed into the breathing system and thus into the patient's airways, thereby inflating his lungs, oxygen and carbon dioxide are then exhaled from the lungs by the passive recoil of the chest of the patient and is returned into the breathing system. A carbon dioxide absorbing means is preferably provided within the breathing system for removing the carbon dioxide from the exhaled gases and the oxygen is then returned to the variable-volume enclosure, thereby expanding it again. The above procedure is repeated intermittently in order to ventilate the patient.

The variable-volume enclosure may be formed with an aperture which is sealed by the one-way valve. The one-way valve of the variable-volume enclosure is usually held closed because the pressure outside the enclosure is not sufficiently greater than that inside the enclosure. However, the oxygen within the enclosure diminishes over a period of time as the patient uses it within his lungs. When the pressure outside the enclosure is greater than the pressure within it by a predetermined margin, the one-way valve is forced open and allows oxygen from the container to enter the enclosure, thus replenishing the oxygen which has been used by the patient.

Alternatively, the container may be formed with an outlet which is in communication with the breathing system, the outlet being sealed by means of a one-way valve, for example, a lightly spring-loaded valve or a water trap valve. When the pressure in the container is greater than that of the breathing system, the one-way valve is forced open and oxygen from the container is permitted to enter the breathing system.

For blood volume measurement, then whilst the apparatus is functioning as described above, a controlled dose of carbon monoxide (or other test gas) is introduced into the breathing system via its inlet such that this carbon monoxide passes into the patient's lungs together with the oxygen. Some of the carbon monoxide crosses the lungs and binds with red blood cells and the remainder is exhaled and recirculated within the breathing system. It usually takes approximately 15 minutes for all of the carbon monoxide to be absorbed by the patient's lungs. A sample of the patient's blood is then tested and the concentration of carboxyhaemoglobin therein is measured such that blood volume may be determined, as in the prior art.

Therefore, the inhalation apparatus of the present invention provides a simple and efficient arrangement for administering a controlled dose of carbon monoxide to a patient for the purpose of blood volume measurement. The patient is ventilated automatically and the oxygen within the ventilating system is topped up automatically, thereby reducing the risk of error. The inlet of the container of the ventilating system may simply be connected to the conventional intensive care ventilating system for the required (e.g. 15 minute) period such that use of the inhalation apparatus is simplified further.

Preferably the variable-volume enclosure comprises a flexible bag, preferably of a bellows-type and preferably having a rigid top wall in which the one-way valve is mounted.

For use as an anaesthetic system, the patient is ventilated in the same manner as described above, the ventilating system periodically topping up the breathing system with oxygen to replace that used by the patient. Further, anaesthetic vapour is injected into the breathing system at an appropriate rate: because the breathing system is closed, none of the anaesthetic vapour is vented to atmosphere or otherwise wasted. Preferably the anaesthetic vapour is injected by a computer controlled syringe.

Preferably for use as an anaesthetic system, the ventilating system can be disconnected from the breathing system and a conventional ventilator connected in its place, for initial de-nitrogenation of the patient: thus, the ventilator alternately supplies oxygen to inflate the lungs, then vents to atmosphere during the recoil exhalation in order that the nitrogen can be exhaled. During this initial period (of typically 15 minutes) anaesthetic is supplied by a conventional anaesthetic unit.

BRIEF DESCRIPTION OF THE DRAWING FIGURES

Embodiments of the present invention will now be described by way of examples only and with reference to the accompanying drawings, in which:

DETAILED DESCRIPTION OF THE DRAWING AND PREFERRED EMBODIMENTS

Figure 1:
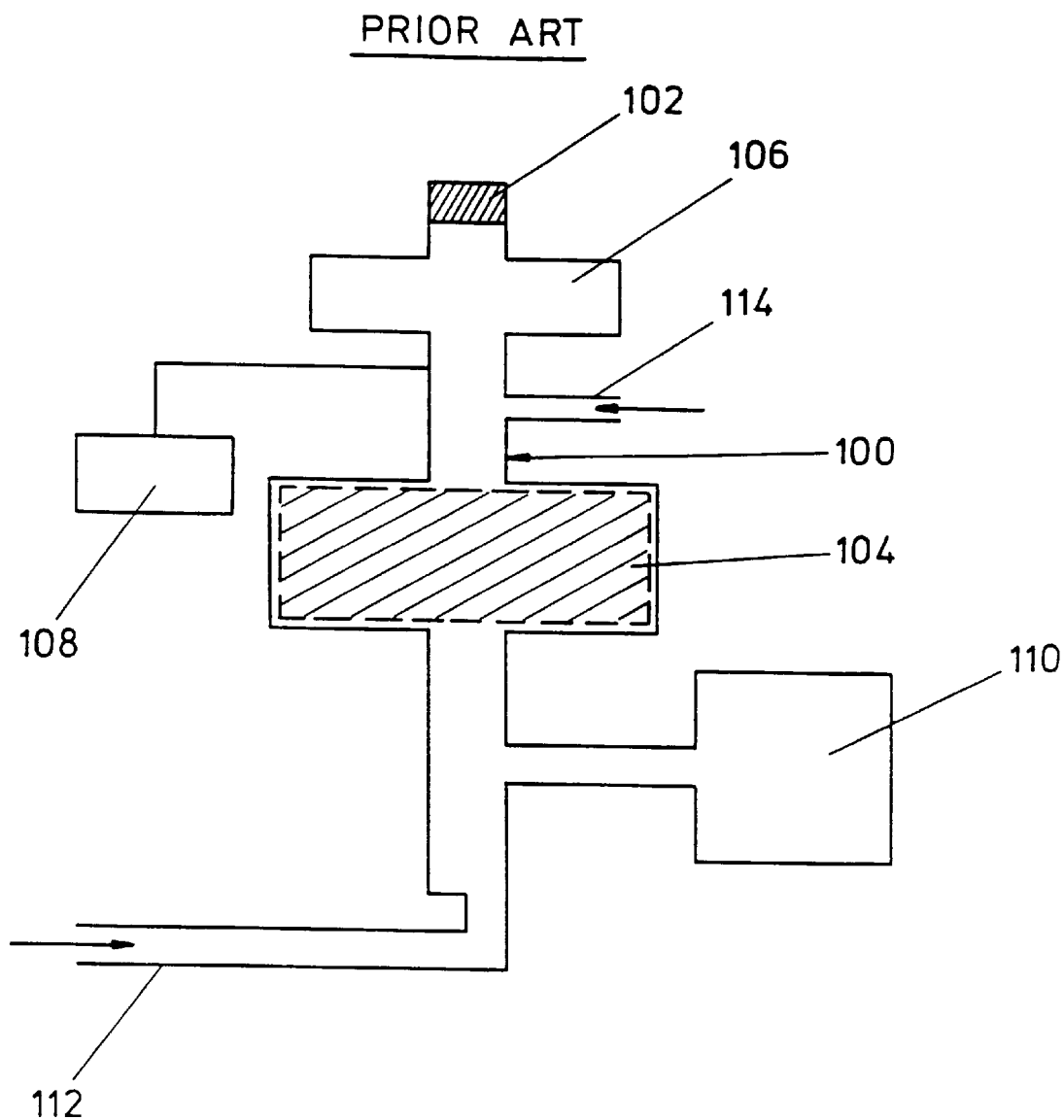
FIG. 1 is a schematic representation of a prior art inhalation apparatus for administering oxygen and a small quantity of carbon monoxide to a patient for the purpose of blood volume measurement.
Figure 2:
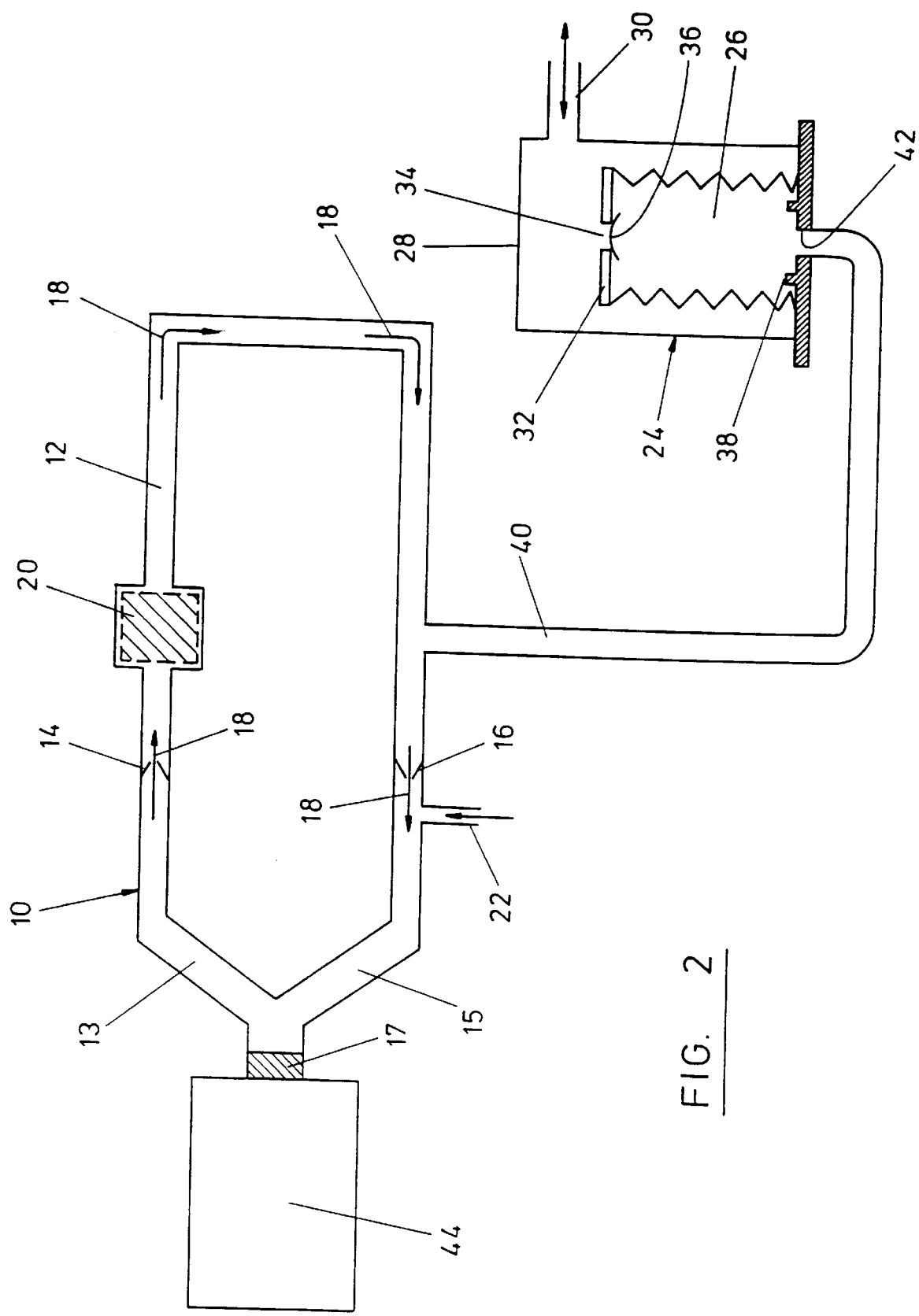
FIG. 2 is a schematic representation of an inhalation apparatus in accordance with the present invention, for administering oxygen and a small quantity of carbon monoxide to a patient.

Referring to FIG. 2 of the drawings, there is shown an apparatus in accordance with the invention and used in the measurement of the volume of blood of a patient. The apparatus comprises a closed circuit breathing system 10 in which a pipe 12 forms a circuit or circle including a first arm 13 and a second arm 15 with a connector 17 provided at a common point between the two arms 13, 15. One-way valves 14, 16 are provided in the first and second arms 13, 15 respectively, allowing gas flow around the circuit in one direction only, as indicated by the arrows 18. A $CO_2$ absorber 20, for example comprising a canister containing soda lime crystals, is provided in the first arm 13 of the circuit, downstream of the one-way valve 14. The second arm 15 is formed with an inlet 22 having a one-way valve (not shown).

The apparatus of FIG. 2 further comprises a 'bag in bottle' ventilating system 24 which consists of a bellows 26 within a transparent container 28, the bellows 26 being filled with oxygen and the container 28 being formed with an inlet 30. A rigid disc 32 closes at the upper end of the bellows 26, and is formed with an aperture 34 which extends into the bellows 26. The aperture 34 is sealed by a one-way flap valve 36 which is normally held closed because the pressure within the bellows 26 is greater than that outside the bellows 26 by virtue of the weight of the disc 32 which acts down on the oxygen within the bellows 26. 'Bump stops' 38 are provided at the lower end of the container 28.

The closed-circuit breathing system 10 and the ventilating system 24 are joined by a pipe 40 which extends from the breathing circuit into the bellows 26 via an opening 42 formed in the base of the container 28.

Figure 3:
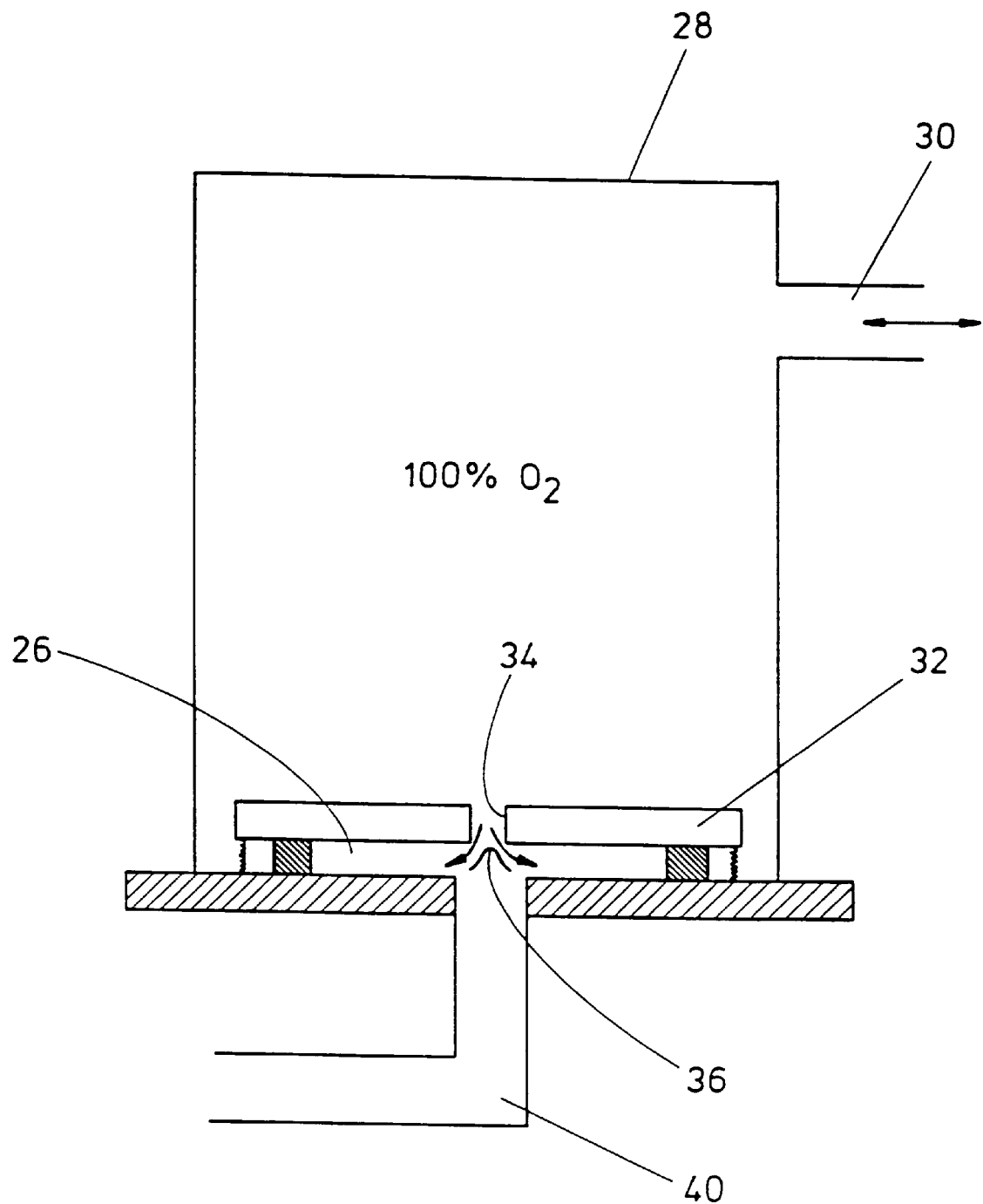
FIG. 3 is a side view of the 'bag in bottle' ventilating system of the apparatus of FIG. 2, when in operation.

In use, initially the system is primed by filling with oxygen so that the bellows 26 is expanded. The connector 17 is connected to the endotracheal tube in the trachea of the patient, indicated diagrammatically at 44, and secured. The inlet 30 of the system 24 is connected to a standard intensive care ventilator (not shown) and this ventilator is adjusted to deliver 100% oxygen. The ventilator alternately pumps oxygen into the container 28, then vents to atmosphere: thus on each cycle, oxygen enters the container 28 via inlet 30 thus increasing the pressure within the container 28 and driving the bellows 26 down. The oxygen within the bellows 26 is accordingly driven into the closed-circuit breathing system 10 via pipe 40, towards the mouthpiece 17 via the one-way valve 16, and into the patient's lungs, causing the latter to expand. Oxygen and carbon dioxide are then exhaled from the lungs due to the passive recoil of the chest of the patient 44, and are introduced into the closed-circuit breathing system 10 via the connector 17. These gases pass through the canister of soda lime 20 via the one-way valve 14 and the carbon dioxide in the exhaled gases is therefore removed such that only oxygen flows from the output of the $CO_2$ absorber and through pipe 40 to re-inflate bellows 26: the cycling of the ventilator is timed so that it has by now switched to vent to atmosphere to permit the bellows to re-inflate. Of course, some of the oxygen used to ventilate the patient 44 is actually taken into the blood of the patient via his lungs. Thus, when oxygen from the ventilator is again driven into the container 28 and the bellows 26 is driven down, oxygen from the bellows 26 is used to replace the oxygen used in the patient's lungs and the procedure described above is repeated. Oxygen is taken from the breathing system 10 by the patient 44 at an average rate of approximately 250 ml per minute. The volume of oxygen within the bellows 26 is therefore progressively reduced and the bellows slowly migrates downwards in the container 28 with each breath, until eventually during a downstroke, it abuts the base. When this occurs, towards the end of the 'drive' part of the ventilator cycle, the pressure outside the bellows 26 becomes greater than that within it by a sufficient amount that the one-way valve 36 is caused to open, thereby allowing oxygen from the ventilator into the bellows to automatically replace the oxygen therein according to the needs of the patient 44. This may be more clearly seen in FIG. 3 of the drawings. Thereafter, on each cycle of the ventilator, the bellows abuts the base of the container towards the end of its downstroke, and a small volume of oxygen is forced through the valve 34.

Referring back to FIG. 2, whilst the above procedure is being performed, a known quantity of carbon monoxide (CO), typically 20–50 ml, is injected into the closed-circuit breathing system 10 via inlet 22. The quantity of CO used depends on the bodyweight of the patient 44 and his initial haemoglobin concentration, which is measured before the procedure is started. The CO passes into the patient's lungs together with the oxygen, and a proportion of the CO crosses the lungs and labels the red blood cells. Any CO which is not absorbed by the lungs is exhaled and re-circulated around the breathing system. When the bellows 26 is driven down again, any CO still in the breathing system is again passed into the patient's lungs where a proportion is again absorbed. This procedure is continued until all of the injected carbon monoxide is absorbed by the patient 44 via his lungs, which normally takes approximately 15 minutes.

In order to determine blood volume, a sample of blood is taken from the patient 44 and the concentration of carboxyhaemoglobin is measured using any known method. Blood volume may then be calculated from this concentration using a suitably programmed computer.

There are a number of advantages associated with the apparatus of FIG. 2. Firstly, it is straightforward and convenient to use since, in order to administer the carbon monoxide, the intensive care ventilator may simply be connected to the container 28 instead of to the patient 44: the only setting which need be altered is the percentage oxygen delivered by the ventilator. Another distinct advantage of this system is that it tops itself up with oxygen automatically according to the specific needs of the patient. No CO gas is allowed to escape from the closed-circuit breathing system 10 such that any CO which is not absorbed by the patient is recirculated. This is imperative since any leakage of CO would result in an erroneous result. Blood volume may be measured at frequent intervals using the apparatus and the apparatus may be simply and economically manufactured such that it may be disposable if required. Finally, blood volume measurement using the apparatus may be carried out at any time during the day or night since administration of the CO gas may be performed by any available member of staff and the calculation of blood volume is carried out automatically by a computer.

Figure 4:
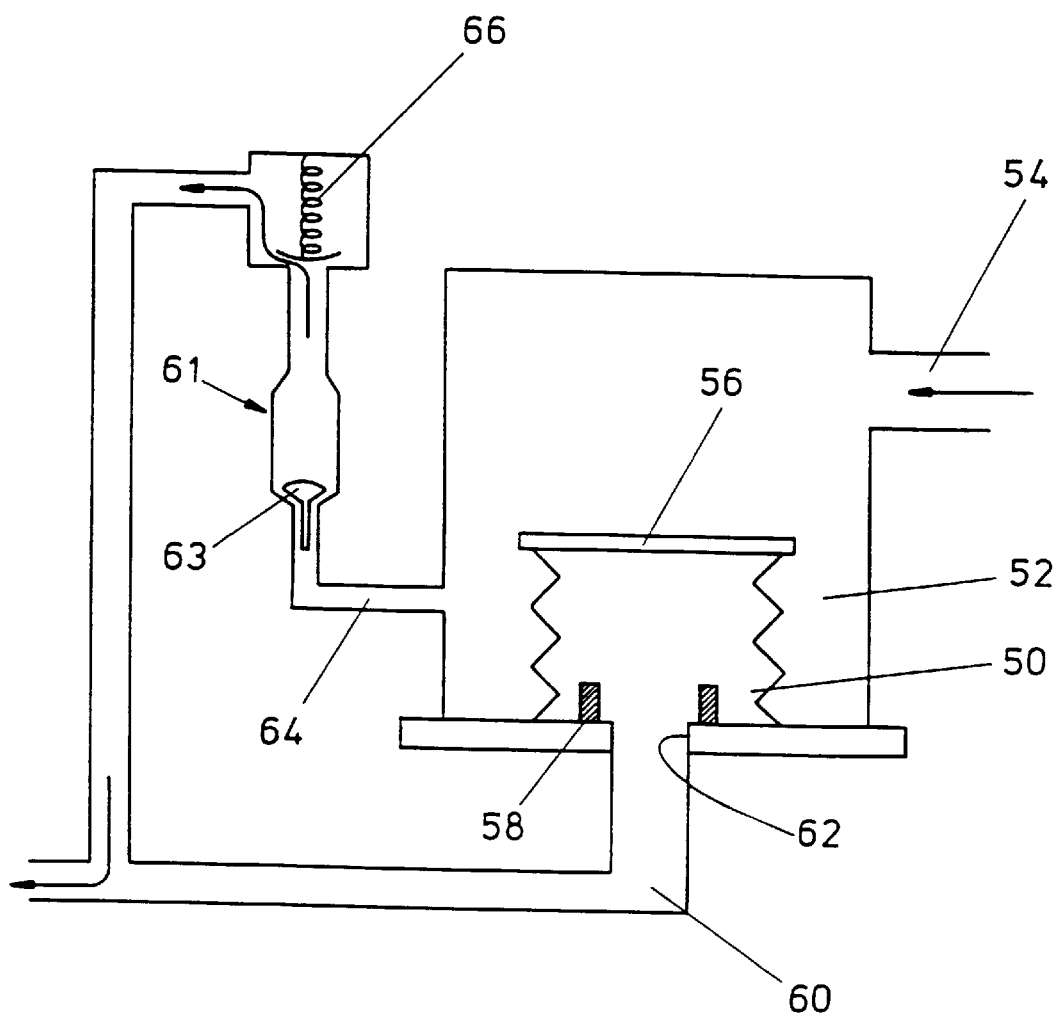
FIG. 4 is a side view of another form of 'bag in bottle' ventilating system for use in the inhalation apparatus of FIG. 2.

Referring to FIG. 4 of the drawings, there is shown an alternative 'bag in bottle' ventilating arrangement again comprising a bellows 50 within a transparent container 52, the bellows 50 being filled with oxygen and the container 52 being formed with an inlet 54. A rigid disc 56 is again provided at the upper end of the bellows, and bump stops 58 are provided at the lower end of the container 52. The 'bag in bottle' arrangement is joined to the closed circuit breathing system by means of a pipe 60 which extends from the breathing circuit into the bellows 50 via an opening 62 formed in the base of the container 52. However, in this arrangement, no aperture is formed in the disc 56. Instead, a second outlet 64 is provided from the transparent container 52 to the pipe 60, and a lightly spring-loaded valve 66 is provided downstream of the container 52 which seals the outlet 64 under normal circumstances. When on each cycle the bellows 50 drops to abut the bump stops 58, the pressure within the transparent container 52 becomes greater than that in the pipe 60, thereby causing the valve 66 to open and allowing oxygen to flow from the container 52 to the closed-circuit breathing system, in the manner described above for FIGS. 2 and 3. A further feature shown in FIG. 4 is a device 61 connecting to the tube 64 to the valve 66: device 61 includes a member 63 which is lifted off its seat each time oxygen flows through the tube 64 and valve 66, to give a visual confirmation that the system is operating correctly.

Figure 5:
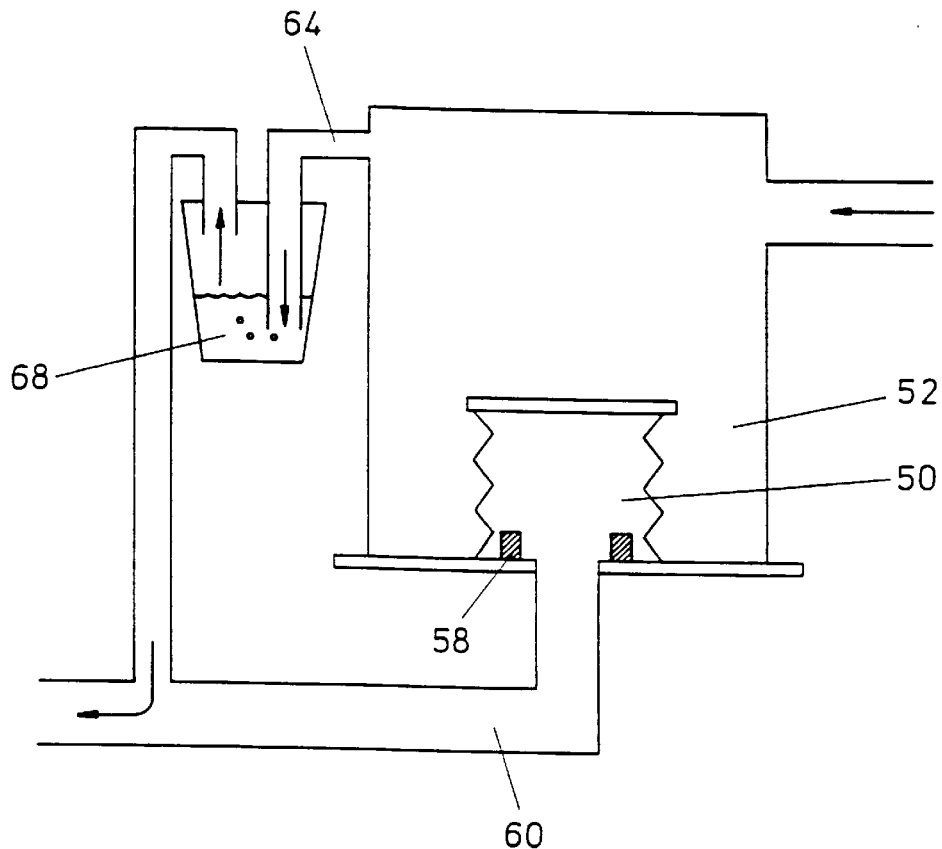
FIG. 5 is a side view of a third form of 'bag in bottle' ventilating system for use in the inhalation apparatus of FIG. 2.

FIG. 5 shows a similar ventilating system in which the outlet 64 of the container 52 is sealed by a water trap valve 68. As before, when the bellows 50 abuts the bump stops 58, the pressure within the container 52 exceeds that in the pipe 60 and oxygen from the container 52 is permitted to enter the pipe 60 via the valve 68, thus continuing to ventilate the patient. The use of a water trap valve 68 has the advantage that such a valve opens and shuts by means of a low pressure gradient and does not leak. Thus, any leak of gas back to the container 52 will always be detected.

Figure 6:
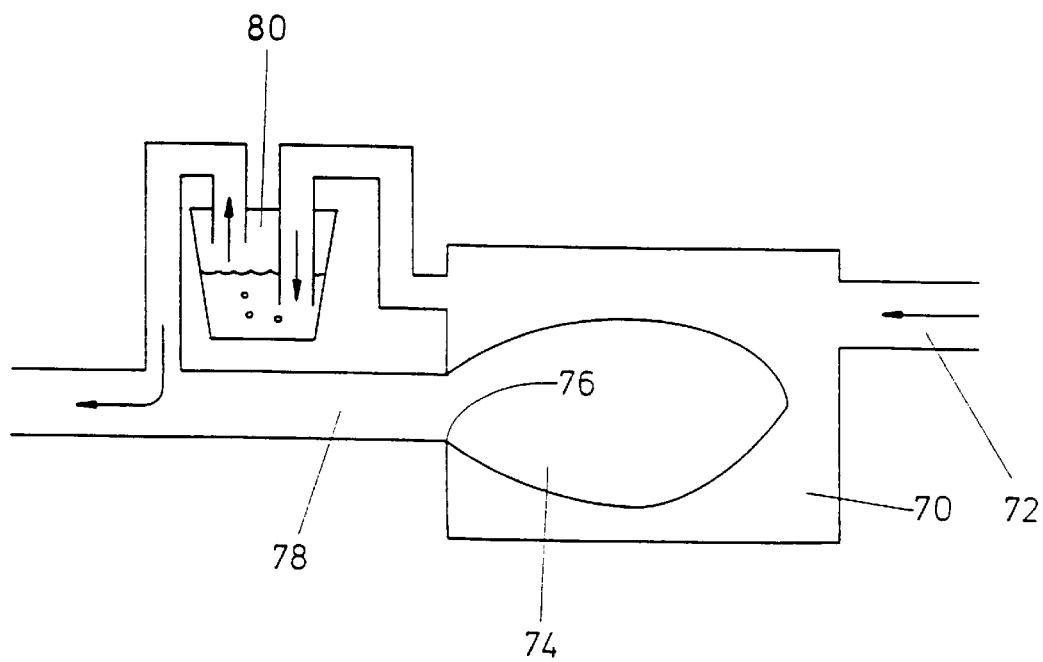
FIG. 6 is a side view of a fourth form of 'bag in bottle' ventilating system.

FIG. 6 shows another 'bag in bottle' ventilating arrangement which comprises a transparent container 70 having an inlet 72 for connection to a ventilator, as before. However, instead of a bellows, a rubber bag 74 filled with oxygen is provided over an outlet 76 formed in the container 70 to which is connected a pipe 78 leading to the breathing system. The system operates as described above. However, in this case, the absence of oxygen within the bag 74 is indicated by the collapse of the bag 74. The pressure within the container 70 is then greater than that in the pipe 78 leading to the closed- circuit breathing system and the difference in pressure causes the valve 80 to open, thereby allowing oxygen to flow from the container 70 into the pipe 78 and therefore into the breathing system. The ventilating arrangement of FIG. 6 may be made relatively cheaply and can therefore be made fully disposable which is convenient and hygienic.

Figure 7:
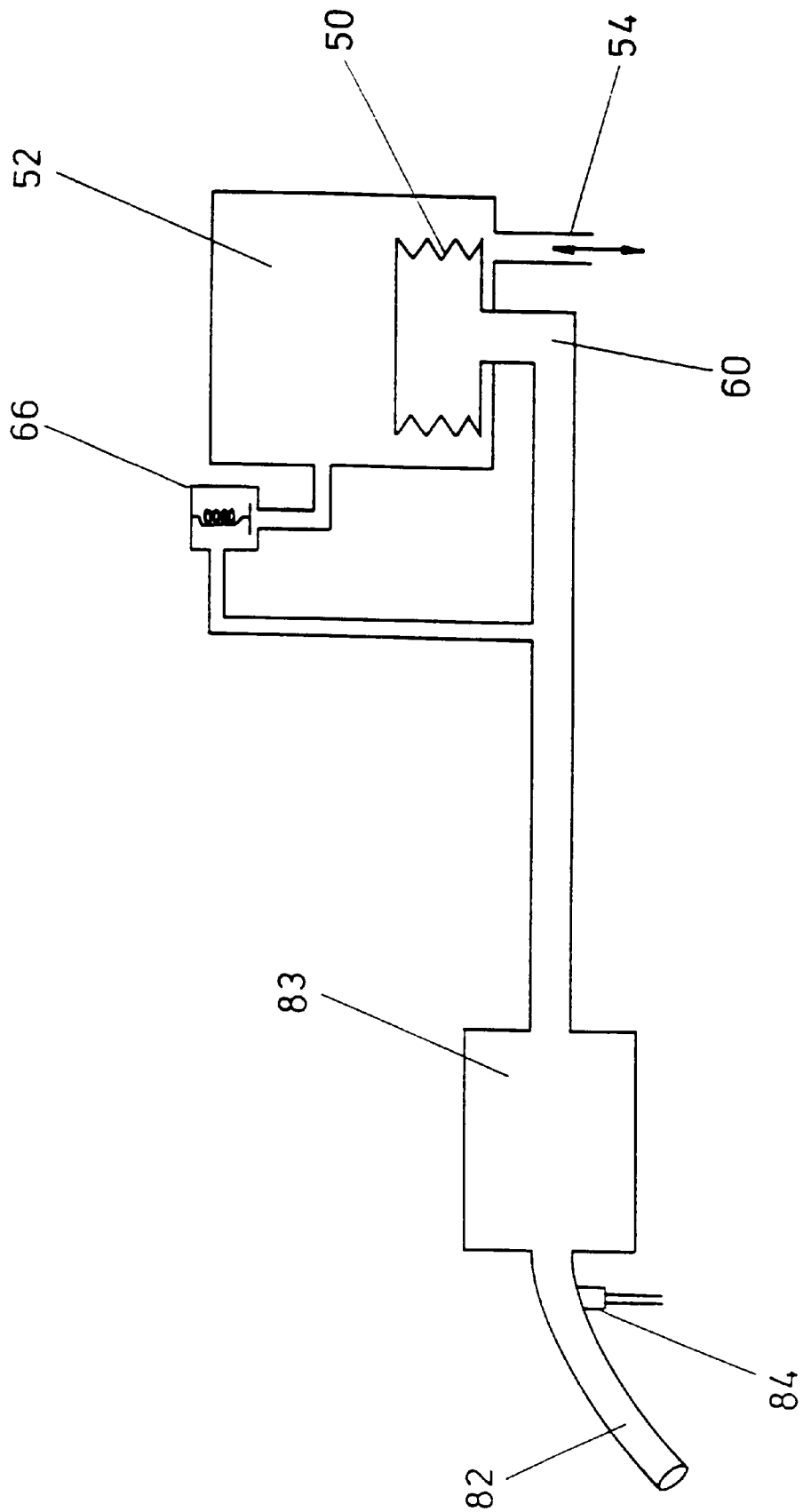
FIG. 7 is a schematic representation of a second embodiment of inhalation apparatus in accordance with the present invention, when used for administering oxygen and a small quantity of carbon monoxide to a patient.

FIG. 7 shows an apparatus in a preferred form for use in blood volume measurement. The apparatus comprises a short pipe 82 connectable at one end to the endotracheal tube and connected at its other end to a vessel 83 containing a carbon dioxide absorber e.g. soda lime. The vessel 83 is connected to a ventilating arrangement, shown here as corresponding to arrangement of FIG. 4: however, a ventilating arrangement as shown in FIGS. 2 and 3, or FIG. 5, or FIG. 6 may be used instead. The breathing system of FIG. 7 is accordingly of a 'to-and-fro' nature, in which oxygen flows to-and-fro along the pipe connecting the endotracheal tube to the ventilating arrangement, through the carbon dioxide absorber. The pipe 82 is provided with a valve 84 to enable the injection of the required dose of carbon monoxide: it is advantageous that the carbon monoxide is accordingly injected close to the patient; preferably the carbon monoxide is injected during the patient's inspiration.

Figure 8:
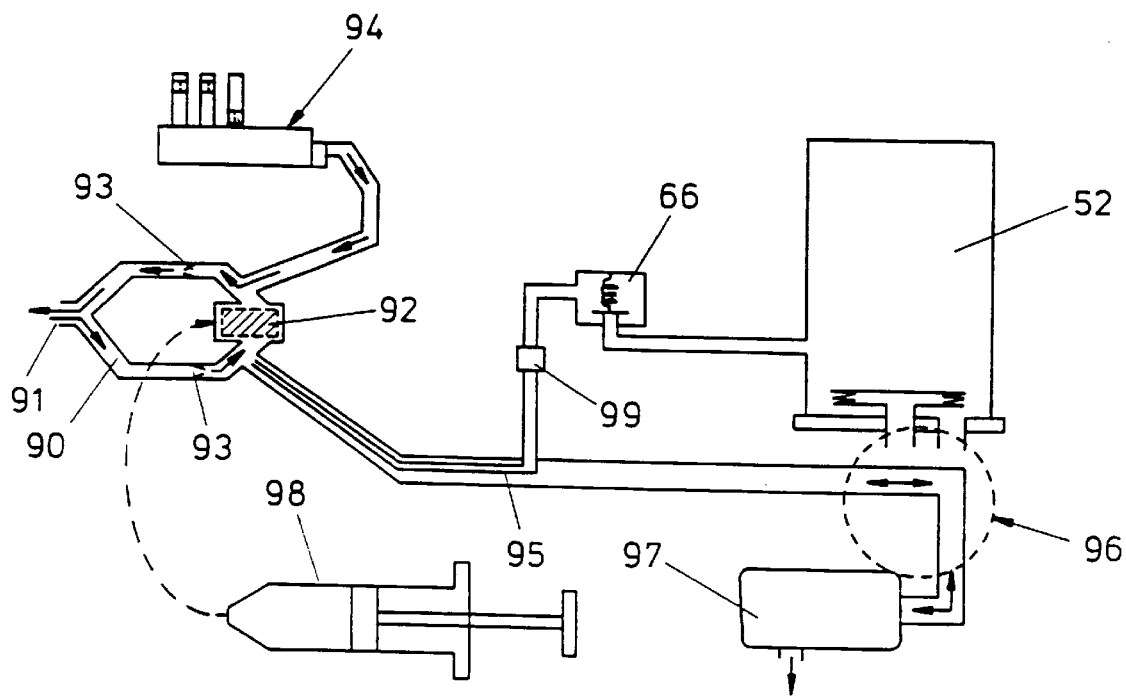
FIGS. 8 and 9 are schematic representations of a third embodiment of inhalation apparatus in accordance with the present invention, when used to form a closed-circuit anaesthetic system, FIG. 8 showing the apparatus configured for initial de-nitrogenation of the patient.
Figure 9:
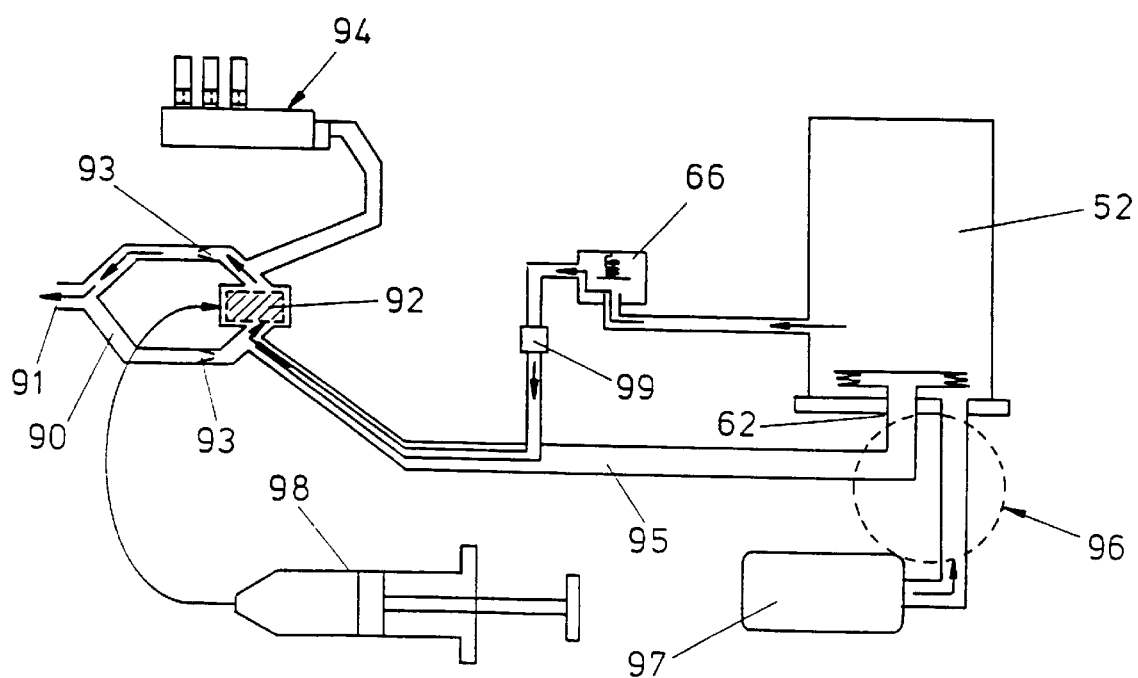

FIGS. 8 and 9 show an apparatus in accordance with the invention, to provide a fully closed circle anaesthetic system. The apparatus comprises a closed circuit 90 having a port 91 for connection to the endotracheal tube and including a vessel 92 containing a carbon dioxide absorber e.g. soda lime, and one-way valves 93. A conventional anaesthetic unit 94 is connected into the circle upstream of one of the valves 93 and a ventilating tube 95 is connected into the circle downstream of the other valve 93, on the opposite side of the carbon dioxide absorber. Ventilating tube 95 is coupled to a ventilating system, which may be as shown in any of FIGS. 2 and 3, FIG. 4, FIG. 5 or FIG. 6. However, a valve 96 enables the ventilator 97 to be connected either to the bellows container 52 or directly to the ventilating tube 95.

In use of the apparatus, and as shown in FIG. 8, firstly the valve 96 is operated to connect the ventilator 97 to the tube 95. The ventilator 97 now acts in conventional manner, supplying oxygen to the circle and venting exhaled gas to atmosphere: at the same time, a predetermined mixture of anaesthetic vapour and oxygen is supplied to the patient from the unit 94. During this initial phase, the nitrogen which is dissolved in the patient's blood diffuses out through the lungs and is exhaled. After about 15 minutes, most of this nitrogen will have been removed from the patient's body.

The valve 96 is then operated to connect the ventilator 97 to the bellows container 52 and the tube 95 to the bellows outlet 62, as shown in FIG. 9. The system is primed before use: the container 52 is flushed with oxygen prior to the start of the anaesthetic procedure; with the apparatus configured as shown in FIG. 9, all of the first bolus or quantity of oxygen now supplied to the container 52 with flow through valve 66 into the circle, thus inflating the patient's lungs— the recoil of the patient's chest and consequent exhalation inflates the bellows. The system then continues to operate, to the system continues, to supply oxygen to the patient, as described above for FIGS. 2 to 6. However, the unit 94 is turned off, and instead a volatile anaesthetic is delivered from a syringe 98 into the circle, possibly into the soda lime vessel 92, under computer control.

This closed-circuit anaesthetic arrangement continues for the duration of the operative procedures on the patient. It will be appreciated that because the circuit is fully closed, there is no risk of the volatile anaesthetic leaking into the atmosphere and so being wasted.

Advantageously, a flow meter may be connected at 99, in the pipe from the valve 66 to the ventilating tube 95, to enable the oxygen consumption of the patient to be measured or monitored.

Preferably as shown in FIGS. 8 and 9, the oxygen delivery pipe from valve 66 runs within the ventilating tube 95 in order to deliver the oxygen as close as possible to the closed circuit 90, and therefore as close as possible to the patient.

I claim:

1. An inhalation apparatus, comprising a closed breathing system having a port for coupling to a patient and an inlet for receiving gas or vapor, and a ventilating system for supplying oxygen to said breathing system and comprising a sealed variable volume enclosure situated within a container, said container having an inlet for receiving a supply of oxygen, outside of said enclosure, the interior of said enclosure being in communication with said closed breathing system and said closed breathing system being in communication with said oxygen supply via a one-way valve arranged for allowing oxygen to pass from said oxygen supply to said closed breathing system when the pressure of said oxygen supply exceeds that within said breathing system.

2. An inhalation apparatus as claimed in claim 1, in which said closed breathing system comprises a pipe, one end of which forms said port for coupling to the patient, and the opposite end of which is connected to said ventilating system.

3. An inhalation apparatus as claimed in claim 2, in which said pipe includes a compartment containing a carbon dioxide absorbing substance.

4. An inhalation apparatus as claimed in claim 1, in which said breathing system comprises a pipe forming a closed circuit provided with said port and connected to said ventilating system, and also including one-way valves to ensure a one-way circulation of gases around said closed circuit pipe.

5. An inhalation apparatus as claimed in claim 4, in which said closed circuit duct includes a compartment containing a carbon dioxide absorbing substance.

6. An inhalation apparatus as claimed in claim 4, further comprising means for injecting an anaesthetic vapor into said closed-circuit via said inlet.

7. An inhalation apparatus as claimed in claim 6, in which said inlet is formed into said compartment containing a carbon dioxide absorbing substance.

8. An inhalation apparatus as claimed in claim 6, further comprising an anaesthetic unit for supplying anaesthetic gas into said closed-circuit pipe.

9. An inhalation apparatus as claimed in claim 4, in which the interior of said container, outside of said enclosure, communicates with said breathing system via a tube having one end connected to said one-way valve and its other end in communication with said closed-circuit pipe.

10. An inhalation apparatus as claimed in claim 1, comprising a flow meter to measure or monitor the flow of oxygen from the interior of said container to said closed breathing system.

11. An inhalation apparatus as described in claim 1, in which said variable-volume enclosure comprises a bellows.

12. An inhalation apparatus as claimed in claim 11, in which said one-way valve, communicating the interior of said container, outside of said enclosure, with said closed breathing system, is formed in an end wall of said bellows.

13. An inhalation apparatus as claimed in claim 11, in which said one-way valve is provided in a passage coupled at one end to said container and communicating at its other end with said closed breathing system.

14. An inhalation apparatus as claimed in claim 11, arranged so that said one-way valve will open each time said bellows become fully contracted if the pressure of said oxygen supply exceeds that within said breathing system.

* * * * *